(12) United States Patent
Nagano

(10) Patent No.: US 10,309,913 B2
(45) Date of Patent: Jun. 4, 2019

(54) PATTERN INSPECTION METHOD USING CHARGED PARTICLE BEAM

(71) Applicant: TOSHIBA MEMORY CORPORATION, Tokyo (JP)

(72) Inventor: Osamu Nagano, Nagoya Aichi (JP)

(73) Assignee: Toshiba Memory Corporation, Tokyo (JP)

( * ) Notice: Subject to any disclaimer, the term of this patent is extended or adjusted under 35 U.S.C. 154(b) by 0 days.

(21) Appl. No.: 15/909,485

(22) Filed: Mar. 1, 2018

(65) Prior Publication Data

US 2018/0335396 A1 Nov. 22, 2018

(30) Foreign Application Priority Data

May 19, 2017 (JP) ................. 2017-100136

(51) Int. Cl.
*H01J 37/26* (2006.01)
*H01J 37/28* (2006.01)
*H01J 37/244* (2006.01)
*G01N 23/2251* (2018.01)

(52) U.S. Cl.
CPC ........ *G01N 23/2251* (2013.01); *H01J 37/244* (2013.01); *H01J 37/265* (2013.01); *H01J 37/28* (2013.01); *H01J 2237/24514* (2013.01); *H01J 2237/2817* (2013.01)

(58) Field of Classification Search
CPC .. G01N 23/2251; H01J 37/244; H01J 37/265; H01J 37/28; H01J 2237/24514; H01J 2237/2817

USPC ................. 250/306, 307, 310, 311
See application file for complete search history.

(56) References Cited

U.S. PATENT DOCUMENTS 8,384,051 B2   2/2013   Ozawa

FOREIGN PATENT DOCUMENTS

| JP | 2002352763 A | 12/2002 |
| JP | 2006245176 A | 9/2006 |
| JP | 2012109477 A | 6/2012 |
| JP | 2014238962 A | 12/2014 |

*Primary Examiner* — Nicole M Ippolito
*Assistant Examiner* — Hanway Chang
(74) *Attorney, Agent, or Firm* — Kim & Stewart LLP

(57) ABSTRACT

A pattern inspection method includes scanning a plurality of patterns on a substrate with N charged particle beams and detecting secondary electrons respectively generated from each of the plurality of patterns to acquire N SEM images, determining a distribution of gray level values for each of the acquired N SEM images, selecting M gray levels from the distributions of the N gray levels, selecting a first gray level value from a first one of the M distributions, and comparing it to the corresponding first gray level value of the of the other M−1 distributions, and determining that an abnormality has occurred in the charged particle beam corresponding to the first one of the M distributions when the difference between the first value of the first one of the M distributions and the other M−1 distributions is greater than a predetermined threshold value.

20 Claims, 3 Drawing Sheets

PATTERN INSPECTION METHOD USING CHARGED PARTICLE BEAM

CROSS-REFERENCE TO RELATED APPLICATION

This application is based upon and claims the benefit of priority from. Japanese Patent Application No. 2017-100136, filed May 19, 2017, the entire contents of which are incorporated herein by reference.

FIELD

Embodiments described herein relate generally to a defect inspection method using a charged particle beam (e.g., electron beam).

BACKGROUND

Attention is paid to multi-beam SEM devices that simultaneously scan a single beam scanning electron microscope (hereinafter, appropriately referred to as an SEM) device with a plurality of electron beams to acquire an SEM image.

DETAILED DESCRIPTION

Embodiments provide a defect inspection method for detecting an abnormality occurring in a specific electron beam among a plurality of electron beams of a multi-beam SEM device.

In general, according to one embodiment, there is provided a pattern inspection method including scanning a plurality of patterns on a substrate with N charged particle beams and detecting secondary electrons respectively generated from each of the plurality of patterns to acquire N SEM images, determining a distribution of gray level values for each of the acquired N SEM images, selecting M, where M is a whole number equal to or less than N, gray levels from the distributions of the N gray levels for each of the acquired N SEM images, selecting a first gray level value from a first one of the M distributions, and comparing it to the corresponding first gray level value of the of the other M−1 distributions, and determining that an abnormality has occurred in the charged particle beam corresponding to the first one of the M distributions when the difference between the first value of the first one of the M distributions and the first value of the other M−1 distributions is greater than a predetermined threshold value.

First Embodiment

Figure 1:
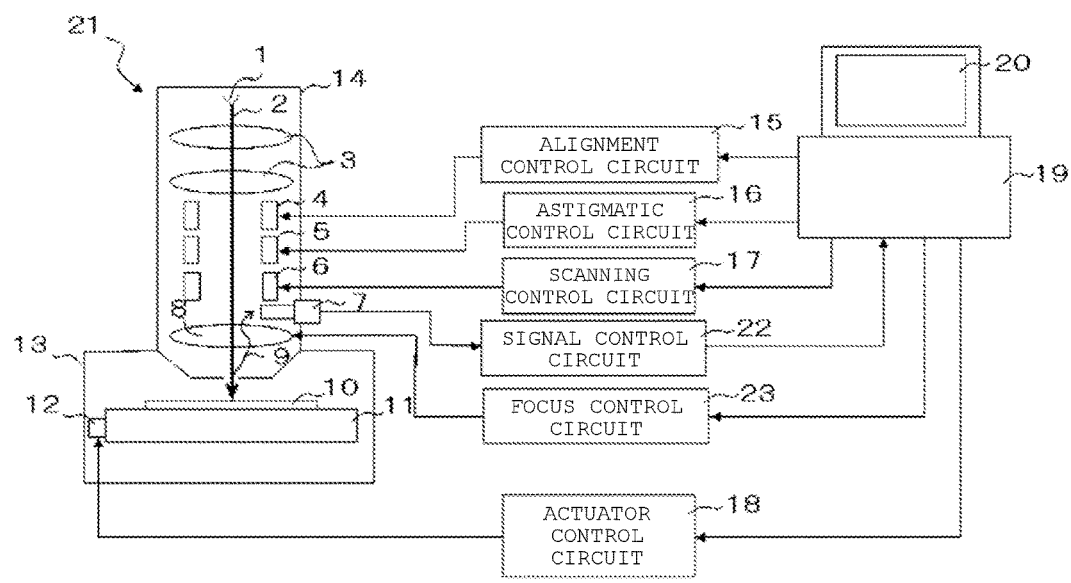
FIG. 1 shows a defect inspection device using a single beam SEM device.

FIG. 1 shows a defect inspection device using a single beam SEM device in order to describe a portion of a configuration of an exemplary embodiment of the present disclosure. A substrate such as a semiconductor wafer 10 is loaded onto a stage 11 of the defect inspection device, which also includes a scanning electron microscope 21, a computer 19, and a monitor 20. The scanning electron microscope 21 includes an electron gun 1 provided in the upper portion of a lens-barrel 14, a condenser lens 3, an aligner 4, an astigmatism corrector 5, a deflector 6, a detector 7, and an objective lens 8. Electron beams 2 radiated from the electron gun 1 are emitted toward the wafer 10 through the condenser lens 3 and the objective lens 8. In addition, the electron beams 2 are appropriately deflected by the deflector 6 under the control of a scanning control circuit 17 controlled by a computer 19. Secondary electrons 9 generated from the wafer 10 as a result on the impingement thereof of the emitted electron beam 2 are detected by the detector 7, a gain is adjusted by a signal control circuit 22 controlled by the computer 19, and a detection signal thereof is input to the computer 19 from the signal control circuit 22. The computer 19 functions as a sample image forming unit that forms a sample image by appropriately performing image processing of the detection signal, and a result of the image processing is output to the monitor 20. The aligner 4 is operated by an alignment control circuit 15 controlled by the computer 19, and the electron beams 2 are deflected by the aligner 4 and are adjusted so that the electron beams 2 pass through the lens axis of the objective lens 8.

The defect detection device operates the objective lens 8 using the focus control circuit 23 controlled by the computer 19 so that the focus of the electron beams 2 on the wafer 10 is adjusted, and similarly operates an astigmatism corrector 5 by an astigmatic control circuit 16 controlled by the computer 19 so that the astigmatism of the electron beams 2 on the wafer 10 is corrected.

The stage 11 is movable in the in the plane of the surface of the substrate, using a control signal input to the actuator 12 from an actuator control circuit 18 controlled by the computer 19.

The computer 19 performs pattern (defect) inspection using an acquired SEM image of a pattern. A pattern inspection system to be mainly used is a Cell comparison system in which, in a repeated pattern within a memory cell each of which should have an identical pattern, i.e., they are purportedly identical, a difference in the pattern from images of the same region of adjacent memory cells is determined, and a determination result indicating a defect is obtained in the case where the difference between the patterns exceeds a threshold value. In a random pattern outside the memory cell, a die comparison system in which inspection is performed by comparing patterns between adjacent dies with each other is mainly used. In a case where a determination result indicating a defect is obtained, defect information such as defect coordinates and a defect image are output.

The inspection method based on the SEM system attains superiority over the inspection method based on an optical system having an optical microscope technique applied thereto in that defect detection sensitivity is extremely high because of a high resolution. In addition, there is also an advantage in that an electrical defect of a circuit pattern including the inside (an underlying lower layer) of the pattern can be detected by obtaining a Voltage Contrast (VC) image.

However, a single beam SEM device has a problem in that the inspection time is extremely long because beam scanning takes a long time in view of the principle thereof. In order to solve this problem, a technique (referred to as a multi-beam technique/multi-column technique) for acquiring a SEM image having a wide area in a short period of time, by simultaneously performing scanning with a plurality of electron beams, is proposed. A technique for simultaneously performing scanning with a plurality of electron beams is referred to as a multi-beam technique, and particularly, a technique in which one or a plurality of electron beams are included in each of a plurality of columns (lens-barrels) is referred to as a multi-column technique. However, both the techniques will be hereinafter collectively referred to as a multi-beam technique.

In the related art, the state or condition of an electron beam is confirmed through the following adjustment process and management process before an inspection process is started. First, gain adjustment and contrast adjustment are performed on an SEM image acquired in a designated pattern region in an adjustment process so as to adjust the returned SEM image to appropriate brightness, and adjustment of focus correction and stig correction (astigmatism correction) are performed as the next step. Next, in the management process, it is confirmed that each value after the adjustment process satisfies specifications registered in the device in advance, and then the inspection process is started.

However, in a multi-beam SEM device, the SEM device structure is complicated because it is necessary to control a plurality of electron beams, and thus the number of power supplies and the number of parts for controlling the beams increase in response to the number of electron beams. In a case where the number of electron beams is increased to several tens or several hundreds, the probability of an abnormality occurring in one of the electron beams during an inspection process increases in proportion to the number of beams used.

Hereinafter, the phrase "abnormality of an electron beam" means that the state of the electron beam deviates from a range (specifications) which is set in advance, due to any cause. Specifically, it means that a management parameter of the electron beam falls outside the preset specifications. Examples of the management parameter to be considered include a gray level average value and a maximum value, which are obtained from a gray level distribution with a gray level for each pixel of the SEM image as a horizontal axis and the number of pixels having the specific gray level value as a vertical axis, the range of the gray level values, and the like.

In addition, in the multi-beam SEM device, since a plurality of electron beams are simultaneously used for scanning, the amount of emission of the electron beams to the wafer per unit time increases in proportion to the number of electron beams, and the quantity of charge on the surface of the wafer rapidly increases with time. Further, a state where a region close to each electron beam is scanned in a short period of time occurs. Therefore, the influence of the charged state of the wafer on each electron beam also changes with time, and thus the degradation of inspection sensitivity due to the deterioration of the image caused not only by a failure of the device but also by charging is also considered in determining an abnormality.

As described above, in the multi-beam SEM device, the number of electron beams is increased, which results in an increase in the probability that an abnormality will occur in at least any one electron beam. However, in an inspection method of the related art, an adjustment process and a management process of an electron beam state and an inspection process thereof are performed as completely separate processes, and thus it is not possible to follow changes in the electron beam state occurring during the inspection process, which leads to a concern that erroneous inspection results can be continuously output. In order to avoid such a problem, a method of performing the adjustment process during the inspection process on a regular basis at time intervals which are set in advance is also proposed. However, the time required to adjust the beams and the resulting processed image is also increased in proportion to the number of beams in the multi-beam system, which leads to a concern that the image acquisition speed, which is the greatest advantage of a multi-beam SEM device, is lost.

A method of monitoring data (an emission current value of the electron gun, the degree of vacuum of a chamber, various power supply voltage values, and the like) of hardware of the device during the inspection process is also proposed. However, an inspection image abnormality occurs not only due to changes in these parameters, but also occur as a result of overlapping of various factors including charging, which results in a problem that the accuracy resulting from monitoring these factors is low. Consequently, in order to simultaneously perform scanning with a plurality of electron beams and to stably obtain a satisfactory SEM image, it is necessary to manage whether or not an abnormality occurs in each of the electron beams, in real time.

Figure 2:
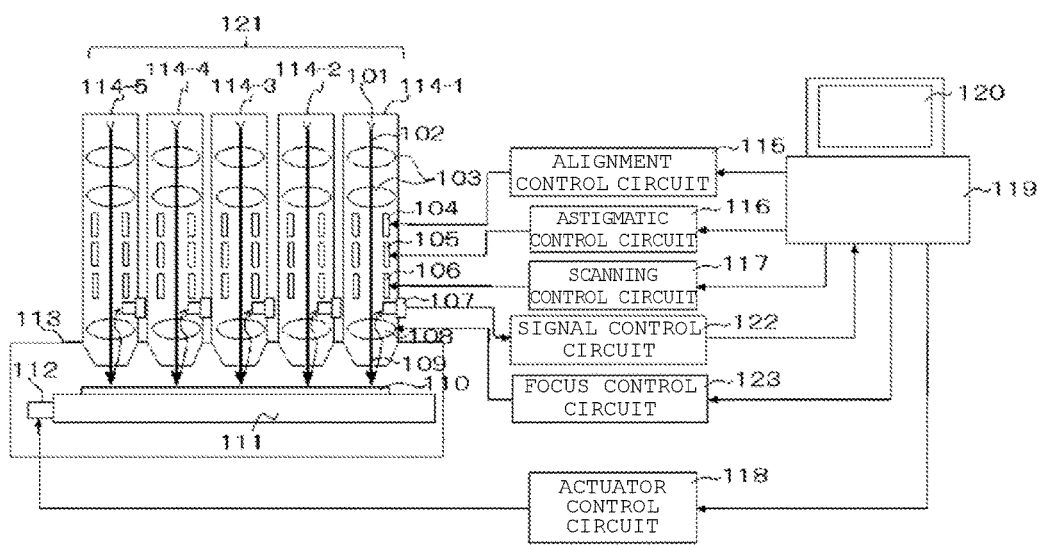
FIG. 2 shows a defect inspection device using a multi-beam SEM device according to an exemplary embodiment of the present disclosure.

FIG. 2 shows a defect inspection device using a multi-beam SEM device according to an exemplary embodiment of the present disclosure. FIG. 2 shows the multi-beam SEM device including five electron beams, and an example of a structure in which five single beam SEM devices are disposed side by side. In the multi-beam SEM device, an alignment control circuit 115, an astigmatic control circuit 116, a scanning control circuit 117, a signal control circuit 122, a focus control circuit 123, and an actuator control circuit 118 are connected to each of lens-barrels 114-1, 114-2, 114-3, 114-4, and 114-5, but circuits other than the circuits connected to the lens-barrel 114-1 are not shown in the drawing. A configuration and operation of each of the lens-barrels are the same as those of the single beam SEM device described in FIG. 1, and the complexity of control of the multi-beam SEM device increases in response to the number of electron beams.

Figure 3:
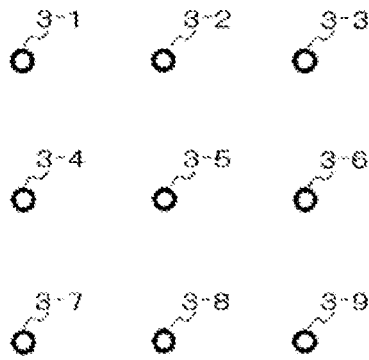
FIG. 3 is a diagram showing a plurality of beams disposed in one lens-barrel in the multi-beam SEM device according to the exemplary embodiment of the present disclosure.

FIG. 2 shows five lens-barrels for convenience of description, but it is also possible to adopt a multi-beam. SEM device in which several tens of lens-barrels or several hundreds of lens-barrels are two-dimensionally arranged in parallel with one another, each having the same configuration, or a structure simplified using a configuration in which a plurality of electron beams are collectively controlled, to avoid complexity proportional to the number of beams. For example, according to a description given with reference to FIG. 3, it is possible to achieve 45 electron beams by locating nine electron beams of electron beams 3-1 to 3-9 in each of the lens-barrels 114-1 to 114-5.

Figure 4:
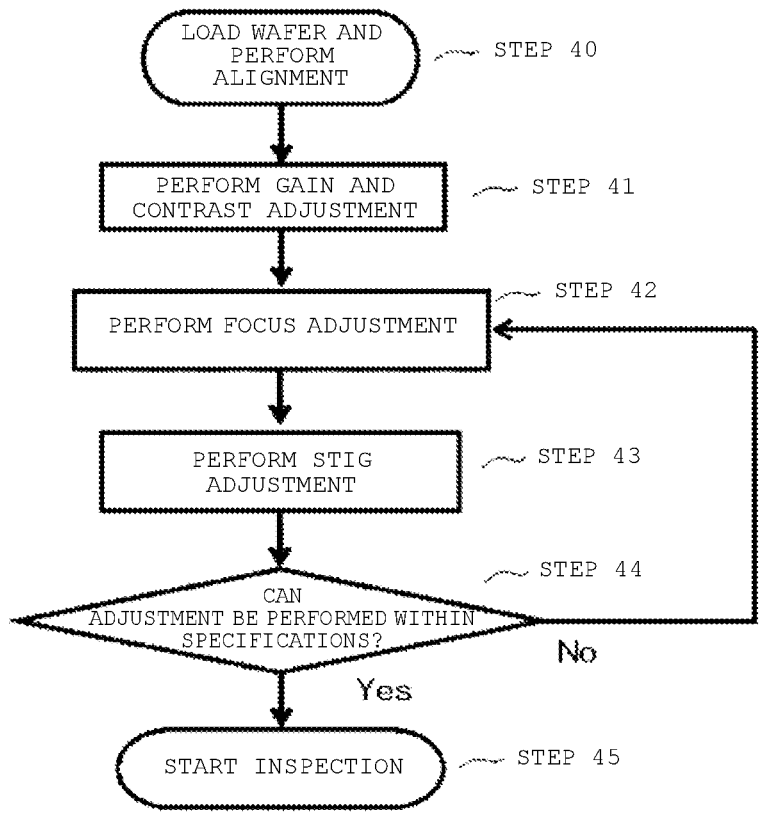
FIG. 4 shows a procedure of an adjustment process and a management process of the multi-beam SEM device according to the exemplary embodiment of the present disclosure.

FIG. 4 shows a procedure of an adjustment process and a management process of the multi-beam SEM device according to the exemplary embodiment of the present disclosure. After the wafer 110 is carried into the device and is aligned on the stage 111 (step 40), the adjustment of the gain and contrast of the detector 107 is performed by the signal control circuit 122 in a pattern for this use designated in advance, on the wafer 110, just before starting inspection, or a pattern for this use designated in advance and located on a calibration substrate disposed at a corner of the stage 111 (step 41), to perform adjustment to the processed image brightness appropriate for the inspection. Thereafter, the focus adjustment (step 42) of the electron beam 102 emitted toward the wafer 110 by the objective lens 108 and the stig adjustment (astigmatism correction, step 43) by the astigmatism corrector 105 are performed. The focus adjustment includes searching for a current value, which is to be input to the objective lens 108, for minimizing the diameter of the beam on the wafer 110, and the stig adjustment includes searching for a voltage (or current) value, which is to be input to the astigmatism corrector 105, for making the shape of the beam on the wafer 110 closest to a completely round shape as possible. The value obtained by the focus adjustment, the value obtained by the stig adjustment, and the obtained SEM image are analyzed by the computer 119. The acquisition of an SEM image is repeatedly performed while changing the value obtained by the focus adjustment and the value obtained by the stig adjustment to perform adjustment to an optimal value by the computer 119 (step 44). In the multi-beam SEM device including the plurality of electron beams, the same sequence is performed for each electron beam. When the computer 119 determines that a result obtained by the adjustment satisfies preset specifications, the inspection of the wafer 110 is started (step 45).

Figure 5:
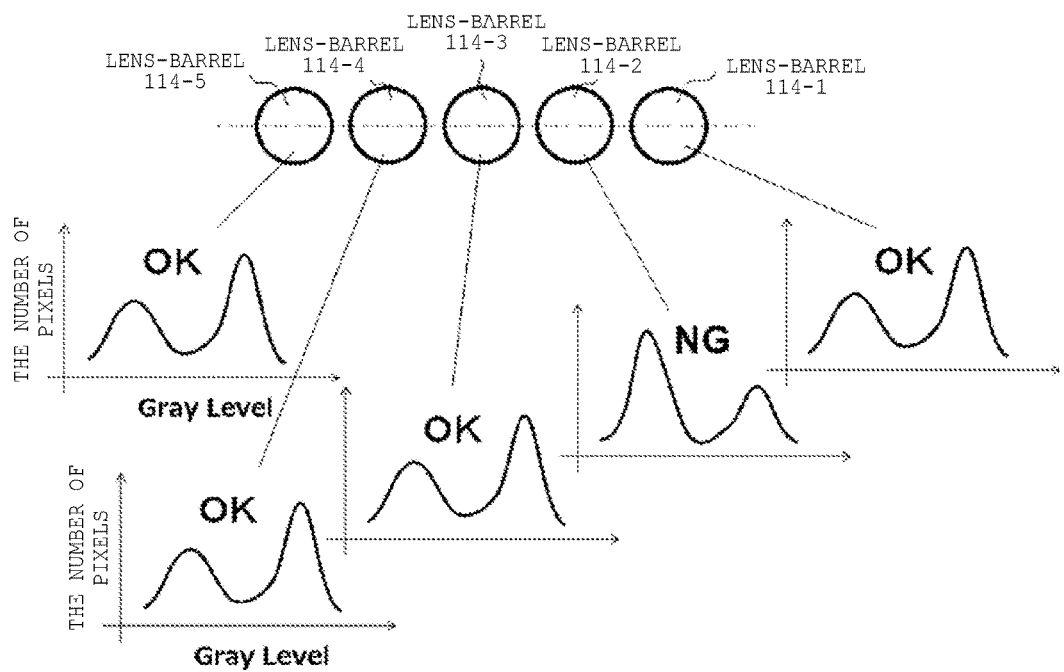
FIG. 5 is a diagram of a defect inspection method according to a first embodiment.

A defect inspection method according to a first embodiment includes a process of comparing statistics, for example the distribution of, measured gray level values in SEM images, which are obtained by performing scanning of the wafer with each electron beam in a multi-beam SEM device including three or more electron beams, with each other, to determine the state of each electron beam. If an odd number of images are chosen, the abnormal one or ones are the number of images less than half the total images that are different from the rest of the images. FIG. 5 shows the defect inspection method according to the first embodiment. From the SEM image acquired from each electron beam of lens-barrels 14-1 to 14-5, a gray level distribution with a gray level for each pixel in a certain fixed region as a horizontal axis, and the number of pixels having the gray level as a vertical axis, is generated. Taking three electron beams as an example, a determination result indicating normality of the beams is obtained in a case where gray scale measurements such as an average value and a maximum value of the gray level which are obtained from the image of any one electron beam are substantially the same as those obtained from the other two electron beams, and a determination result indicating that an abnormality occurs in the electron beam is obtained in a case where a divergence in an average value or a maximum value equal to or greater than a predetermined threshold value occurs in the resulting gray level values for that electron beam. The statistics to be used may include not only the average value and the maximum value but also the range, a peak position, a minimum value, a half-width value, a derivative, and the like of the gray level, as well as by comparing the curves generated as shown in FIG. 5 with each other. When astigmatism occurs, the gray level changes and thus derivatives of waveforms may be compared with each other. Since there is a possibility that variations occur in data acquired from each electron beam, it is possible to improve accuracy by obtaining the statistics relating to the gray levels in an image returned for each beam under conditions designated in a recipe in advance. For example, for each electron beam, statistics acquired from a designated fixed inspection area may be used, or statistics relating to the gray levels in an image returned for each beam acquired from the same inspection region of each designated die may be used.

The determination may be performed in the following sequence in order to prevent the occurrence of an error of the determination due to the influence of a wafer in a specific region where a defect often occurs.

(1) A maximum value and a minimum value of the gray levels are compared with each other, and it is determined that there is no difference therebetween.

(2) In a case where it is determined in (1) that there is no difference therebetween, the comparison between the other statistics relating to the gray levels in an image returned for each beam is performed.

The number of different electron beam gray levels analyzed and used for comparison may be five or seven as long as the number of different electron beam gray levels is three or more. Considering a possibility that a plurality of abnormalities of the electron beams are seen, it is preferable that gray levels obtained from an odd number of electron beams are compared with each other. A process of comparison between electron beams may be performed during a normal defect inspection process at any interval. As the frequency of comparison between the electron beams increases, it is easy to detect an abnormality of a specific electron beam, while a measurement time increases, which leads to a trade-off relationship between speed of measurement and reliability of the resultant measurement.

In a case where a divergence is seen between the above-described statistics for one electron beam and statistics for the other two electron beams, it is considered that it may be difficult to determine whether the divergence is caused by an abnormality of the electron beam or by a defect in a pattern on a wafer being evaluate. However, it is possible to distinguish a divergence due to an electron beam and a divergence due to a pattern from each other by using one or a plurality of methods among the following methods.

A. A gray level obtained from an SEM image of a pattern, such as an alignment pattern on a scribe line, which has a large size and typically does not include a pattern defect is used as a scanning target for comparison of the gray level of images returned for different beams.

B. In a case where an abnormality occurs in gray levels sequentially obtained from an image returned for the same electron beam, the abnormality is determined to be an abnormality of the electron beam.

C. Since there is a difference in a change mode of the gray level between the cause of the difference being the pattern and the cause of the difference being the electron beam (it is considered that there is a greater fluctuation in the cause of the electron beam), comparison between SEM images is performed between images obtained from the returned signal for the same electron beam in a normal defect inspection process in which the magnitude of a threshold value is adjusted. On the other hand, in a process for detecting an abnormality of an electron beam in an example according to the exemplary embodiment of the present disclosure, pieces of data from the returned signal of different electron beams are compared with each other. However, pieces of data from the returned signal of different electron beams may be compared with each other also in a normal defect inspection process depending on measurement conditions. Also in this case, there is a difference in that a threshold value for detecting an abnormality of an electron beam is larger than a threshold value for determining an abnormality in the normal defect inspection process.

In the defect inspection method according to the exemplary embodiment of the present disclosure, in a case where an abnormality is detected in a certain electron beam, defect inspection using the electron beam having the abnormality is terminated at that point in time. With respect to a region scheduled to be inspected using the electron beam and a region in which even the detection of an abnormality is inspected, inspection is performed using another electron beam determined to be a normal electron beam.

Second Embodiment

Figure 6:
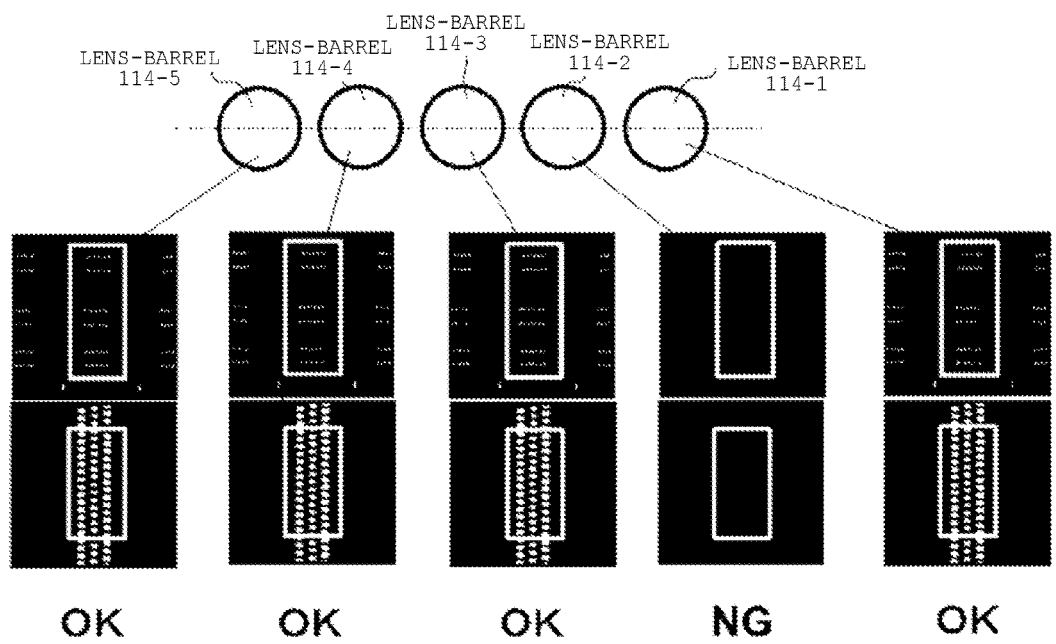
FIG. 6 is a diagram of a defect inspection method according to a second embodiment.

A defect inspection method according to a second embodiment includes a process of managing the state of each electron beam by comparing SEM images, which are obtained by performing scanning with respective electron beams, with each other between the electron beams in a multi-beam SEM device including three or more electron beams. FIG. 6 shows the defect inspection method according to the second embodiment. SEM images acquired from respective electron beams of lens-barrels 14-1 to 14-5 are compared with each other, and it is determined that an abnormality occurs in a case where a difference therebetween is equal to or greater than a predetermined threshold value. Taking three electron beams as an example, an SEM image obtained using any one electron beam is compared with SEM images obtained using two or more of the other electron beams. A determination result indicating normality is obtained in a case where the SEM images as compared with each other are substantially the same, and a determination result indicating that an abnormality occurs in the electron beam is obtained in a case where there is a difference in the SEM images, for example a pattern in the SEM images, equal to or greater than a predetermined threshold value. The number of SEM images obtained using different electron beams and used for comparison may be five or seven as long as the number of SEM images is three or more. Considering a possibility that a plurality of abnormalities of the electron beams are seen, it is preferable that SEM images obtained from an odd number of electron beams are compared with each other. This embodiment is the same as the first embodiment in that a process of comparison between electron beams may be performed during a normal defect inspection process at any intervals.

In a case where a difference is seen between the above-described SEM image for one electron beam and SEM images obtained from the other two electron beams, distinguishing between whether the difference is caused by an abnormality of the electron beam or by an abnormality of a pattern on a wafer to be observed can be performed using one or a plurality of methods among the following methods, similar to the first embodiment.

A. A SEM image of a pattern, such as an alignment pattern on a scribe line, which has a large size and typically does not include a pattern defect is used as a scanning target for comparison of the gray level of images returned for different beams.

B. In a case where an abnormality occurs in SEM images sequentially obtained from an image returned for the same electron beam, the abnormality is determined to be an abnormality of the electron beam.

C. Since there is a difference in a change mode of the SEM image between the cause of the difference being the pattern and the cause of the difference being the electron beam (it is considered that there is a greater fluctuation in the cause of the electron beam), comparison between SEM images is performed between images obtained from the returned signal for the same electron beam in a normal defect inspection process in which the magnitude of a threshold value is adjusted. On the other hand, in a process for detecting an abnormality of an electron beam in an example according to the exemplary embodiment of the present disclosure, pieces of data from the returned signal of different electron beams are compared with each other. However, pieces of data from the returned signal of different electron beams may be compared with each other also in a normal defect inspection process depending on measurement conditions. Also in this case, there is a difference in that a threshold value for detecting an abnormality of an electron beam is larger than a threshold value for determining an abnormality in the normal defect inspection process.

In the defect inspection method according to the exemplary embodiment of the present disclosure, in a case where an abnormality is detected in a certain electron beam, defect inspection using the electron beam having the abnormality is terminated at that point in time. With respect to a region scheduled to be inspected using the electron beam and a region in which even the detection of an abnormality is inspected, inspection is performed using another electron beam determined to be a normal electron beam.

Effects of Exemplary Embodiment of the Present Disclosure

With respect to each of a plurality of electron beams used in a multi-beam SEM device, it is possible to simultaneously perform beam abnormality detection and correction while also performing inspection and to improve the accuracy of an inspection image and the accuracy of inspection and measurement.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A pattern inspection method, comprising:
scanning a plurality of patterns on a substrate with N charged particle beams and detecting secondary electrons respectively generated from each of the plurality of patterns to acquire N SEM images;
determining a distribution of gray level values for each of the acquired N SEM images;
selecting M, where M is a whole number equal to or less than N, gray levels from the distributions of the N gray levels for each of the acquired N SEM images;
selecting a first gray level value from a first one of the M distributions, and comparing it to the corresponding first gray level value of the of the other M−1 distributions; and
determining that an abnormality has occurred in the charged particle beam corresponding to the first one of the M distributions when the difference between the first value of the first one of the M distributions and the first value of the other M−1 distributions is greater than a predetermined threshold value.

2. The pattern inspection method according to claim 1, wherein M is an odd whole number greater than one.

3. The pattern inspection method according to claim 1, wherein the first value is a maximum gray level value in each distribution.

4. The pattern inspection method according to claim 1, wherein the first value is an average of the gray level value in each distribution.

5. The pattern inspection method according to claim 1, wherein the first value is the half-width value of each distribution.

6. The pattern inspection method according to claim 1, wherein the first value is a minimum gray level value in each distribution.

7. The pattern inspection method according to claim 1, wherein the first value is a derivative of the gray level value in each distribution.

8. A pattern inspection method, comprising:
scanning a plurality of patterns on a substrate with N charged particle beams and detecting secondary electrons respectively generated from each of the plurality of patterns to acquire N SEM images used to determine the presence of a defect in the pattern and concurrently;
determining a related gray level value for each of the acquired N SEM images;
selecting M gray levels from the distributions of the N gray levels for each of the acquired N SEM images;
comparing the related gray level value of each of the M gray levels;
determining which related gray level values, from among the M related gray level values, have a similar gray level value within a preset range of deviation of the gray level value, and determining which, if any of the related gray level values from among the M related gray level values have a value outside of a preset range of deviation from the other of the M gray level values; and
stopping use of any charged particle beam corresponding to the gray level value, from among the M gray level values, having a value outside of a preset range of deviation from the other of the M gray level values.

9. The method according to claim 8, wherein the related gray level value is the gray level distribution of a SEM image.

10. The method according to claim 8, wherein the related gray level value is a derivative of the gray level distribution of a SEM image.

11. The method according to claim 8, wherein the related gray level value is the minimum gray level value of a SEM image.

12. The method according to claim 8, wherein the related gray level value is the maximum gray level value of a SEM image.

13. The method according to claim 8, wherein the related gray level value is the half width gray level value of a SEM image.

14. The method according to claim 8, wherein M is an odd whole number greater than one.

15. A pattern inspection method, comprising:
scanning a plurality of patterns on a substrate with N charged particle beams and detecting secondary electrons respectively generated from each of the plurality of patterns to acquire N SEM images useful for determining the presence of a defect in the pattern, and concurrently;
selecting M images from the N SEM images;
comparing a property of an N SEM image with the remaining N−1 SEM images; and
determining whether the property of the selected N SEM image is different from that same property in the remaining N−1 SEM images by more than a preset threshold amount; and
if the property of the selected N SEM image is different from that same property in the remaining N−1 SEM images by more than the preset threshold amount, stopping use of the charged particle beam corresponding to the SEM image having the property which is different from that same property in the remaining N−1 SEM images by more than the preset threshold amount.

16. The pattern inspection method according to claim 15, wherein the property is a pattern in the SEM images.

17. The pattern inspection method according to claim 15, wherein the property is a maximum gray scale value in the SEM images.

18. The pattern inspection method according to claim 15, wherein the property is a minimum gray scale value in the SEM images.

19. The pattern inspection method according to claim 15, wherein the property is a distribution of the gray scale values in the SEM images.

20. The pattern inspection method according to claim 15, further comprising:
after comparing a property of an N SEM image with the remaining N−1 SEM images; and
determining whether the property of the selected N SEM image is different from that same property in the remaining N−1 SEM images by more than a preset threshold amount; and
if the property of the selected N SEM image is different from that same property in the remaining N−1 SEM images by more than the preset threshold amount, stopping use of the charged particle beam corresponding to the selected SEM;
comparing a property of a another of the N SEM image with the remaining N−1 SEM images; and
determining whether the property of the another of the N SEM image is different from that same property in the remaining N−1 SEM images by more than a preset threshold amount; and
if the property of the another N SEM image is different from that same property in the remaining N−1 SEM images by more than the preset threshold amount, stopping use of the charged particle beam corresponding to the another N SEM image.

* * * * *